| United States Patent [19] | [11] Patent Number: 4,740,330 |
|---|---|
| Wang et al. | [45] Date of Patent: Apr. 26, 1988 |

[54] METHOD FOR ALLYLATING AROMATIC HYDROXYL-CONTAINING COMPOUNDS

[75] Inventors: Chun S. Wang; Zeng-kun Liao, both of Lake Jackson, Tex.

[73] Assignee: The Dow Chemical Company, Midland, Mich.

[21] Appl. No.: 903,164

[22] Filed: Sep. 3, 1986

[51] Int. Cl.[4] .................... C09B 11/06; C07C 41/00
[52] U.S. Cl. .................... 260/395; 568/657; 568/572; 568/630; 568/716
[58] Field of Search ............... 568/630, 716, 286, 572; 260/395

[56] References Cited

U.S. PATENT DOCUMENTS

| 3,060,243 | 10/1962 | Ham | 568/716 |
|---|---|---|---|
| 3,842,033 | 10/1974 | Brady et al. | 568/630 |
| 3,974,084 | 8/1976 | Pietzsch et al. | 568/716 |
| 4,127,615 | 11/1978 | Zahir et al. | 568/630 |

FOREIGN PATENT DOCUMENTS

| 58-159436 | 9/1983 | Japan | 568/630 |
|---|---|---|---|
| 58-173118 | 10/1983 | Japan | 568/630 |
| 59-66414 | 4/1984 | Japan | 568/630 |
| 59-105014 | 6/1984 | Japan | 568/630 |
| 59-124905 | 7/1984 | Japan . | |

OTHER PUBLICATIONS

*Chemical Abstract,* vol. 90, No. 22477w, 1979, Akabori et al., "Anion Activation by Polymer-Linked Crown Ether".

*Chemical Abstract,* vol. 92, No. 128506m, 1979, Akabori et al., ", Allylation of Phenoxides by Crown Ethers and Their Polymers.

*Primary Examiner*—Glennon H. Hollrah
*Assistant Examiner*—Raymond Covington

[57] ABSTRACT

The aromatic hydroxyl groups of aromatic hydroxyl-containing compounds can be allylated to greater than 95% conversion by reacting the alkali metal salt of said aromatic hydroxyl-containing compounds with an allyl halide such as allyl chloride in the presence of a polar aprotic solvent such as dimethylformamide. These compounds are useful in preparing epoxy resins containing a low halogen content.

16 Claims, No Drawings

METHOD FOR ALLYLATING AROMATIC HYDROXYL-CONTAINING COMPOUNDS

BACKGROUND OF THE INVENTION

The present invention pertains to a method for allylating aromatic hydroxyl-containing compounds. The allyl ethers of polyphenols are useful for preparing epoxy compounds low in aliphatic halogen content.

Epoxy resins are being used in the electronics industry as components in electrical laminating varnishes, potting compositions encapsulating compositions and the like. Since aliphatic halogen atoms are detrimental to electrical properties, it is desirable to have available for the electronics industry epoxy resins which are extremely low in aliphatic halogen content. The traditional method for preparing aromatic epoxy compounds is to react an aromatic phenolic hydroxyl-containing material with an epihalohydrin and dehydrohalogenating the resultant halohydrin intermediate product with a suitable dehydrohalogenating agent such as an alkali metal hydroxide, carbonate, bicarbonate or the like. However, the resultant epoxy compound usually contains a relatively high amount of aliphatic halogen atoms of either the bound halogen type or the hydrolyzable halogen type or a combination thereof which is often referred to as total halogen content. The aromatic halogen atoms are not usually considered detrimental and are not included in the reporting of the total halogen content since in some instances, such as in electrical laminates, aromatic halogen atoms are desired so as to render the resin more flame retardant.

The present invention provides a method for preparing vicinal epoxy compounds which are very low in aliphatic halogen content rendering them particularly suitable for use in the electronics industry. These low halogen content resins are prepared by the peroxide epoxidation of allyl ethers of aromatic compounds which have been prepared by reacting an allyl halide with an alkali metal salt of an aromatic hydroxyl-containing material in the presence of a polar aprotic solvent so as to convert at least 95% of the aromatic hydroxyl groups to allyl ether groups. When protic solvents such as methanol are employed, conversions of not more than about 85% of the aromatic hydroxyl groups to allyl ether groups is obtained.

SUMMARY OF THE INVENTION

One aspect of the present invention pertains to a process for preparing allyl ethers of aromatic hydroxyl-containing materials which comprises (A) reacting in the essential absence of water other than water produced in the reaction and in the presence of a polar aprotic solvent selected from the group consisting of dimethylformamide, dimethylacetamide, dimethyl sulfoxide, N-methyl pyrrolidinone, tetramethylene sulfone, hexamethyl phosphoramide, and a combination thereof (1) at least one material containing at least one aromatic hydroxyl group with (2) an alkali metal hydroxide, alkali metal carbonate or combination thereof at conditions sufficient to convert at least 95, preferably at least about 98 percent of the aromatic hydroxyl groups to the corresponding alkali metal phenoxide group;

(B) reacting the reaction product mixture produced in (A) above with (3) at least one allyl halide at conditions sufficient to convert at least about 95, preferably at least about 98 percent of the alkali metal phenoxide groups to an allyl ether group; and (C) thereafter recovering the resultant allyl ether product.

DETAILED DESCRIPTION OF THE INVENTION

Suitable aromatic hydroxyl-containing materials which can be employed herein include, for example, those represented by the following formulas I–IV

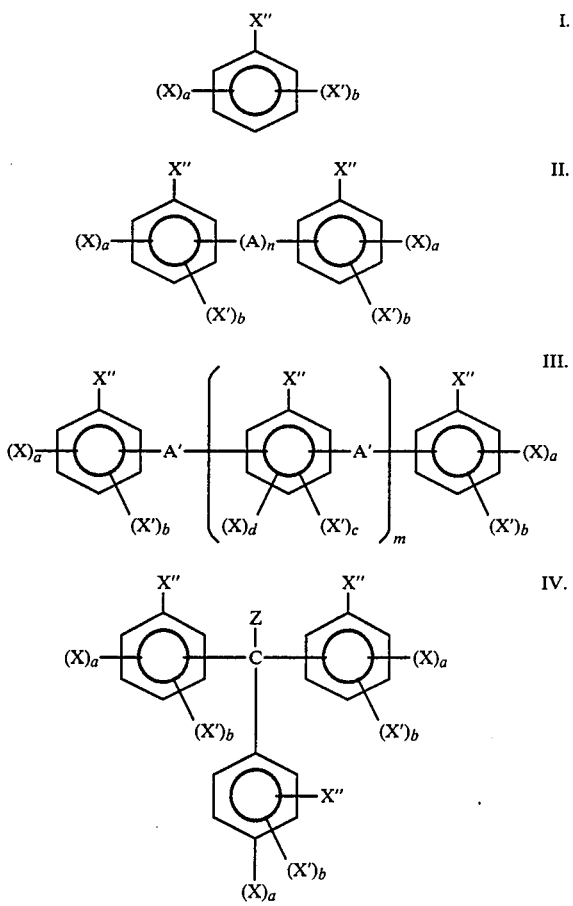

wherein A is a divalent hydrocarbyl group having from 1 to about 25, preferably from 1 to about 10, carbon atoms, a divalent dicyclopentadienyl group, a divalent oligomeric dicyclopentadienyl group, —O—, —S—, —S—S—,

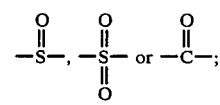

each A' is independently a divalent hydrocarbyl group having from 1 to about 25, preferably from 1 to about 10, carbon atoms, a divalent dicyclopentadienyl group or a divalent oligomeric dicyclopentadienyl group; each X is independently hydrogen, a hydrocarbyl or hydrocarbyloxy group having from 1 to about 10, preferably from 1 to about 6, carbon atoms or a halogen atom, preferably chlorine or bromine; X' is a hydroxyl group; X" is a hydroxyl group; Z is hydrogen or a hydrocarbyl group having from 1 to about 10, preferably from 1 to about 6, carbon atoms; each independently has a value from about 1 to about 3; b and c each has a value of zero or 1; each d independently has a value from 1 to 3; the sum of a+b is 4; the sum of d+c is 3; m has an average value from about zero to about 15, preferably from about zero to about 10 and n has a value of zero or 1.

The term hydrocarbyl as employed herein includes, alkyl, cycloalkyl, aryl, aralkyl, alkaryl, alkenyl and the like. Likewise, the term hydrocarbyloxy as employed herein includes, alkyloxy, cycloalkyloxy, aryloxy, aralkyloxy, alkaryloxy, alkenyloxy and the like.

Particularly suitable aromatic hydroxyl-containing materials include, for example, phenol-formaldehyde novolac resins, o-cresol-formaldehyde novolac resins, p-cresol-formaldehyde novolac resins, resorcinol-formaldehyde novolac resins, combinations thereof and the like. Also suitable aromatic hydroxyl-containing materials include, for example, resorcinol, bisphenol A, bisphenol F, bisphenol K, bisphenol sulfide, bisphenol sulfone, dicyclopentadienyl-bis(2,6-dimethyl phenol), dicyclopentadienyl-bis(o-cresol), dicyclopentadienyl bisphenol, combinations thereof and the like. The polycyclopentadienyl polyphenols and methods for their preparation can be found in U.S. Pat. No. 4,390,680 issued to Donald L. Nelson which is incorporated herein by reference.

Also suitable aromatic hydroxyl-containing materials include, for example, 3,3',5,5'-tetramethyl bisphenol A, 3,3',5,5'-tetramethyl bisphenol F, 3,3',5,5'-tetramethyl bisphenol K, 3,3',5,5'-tetramethyl bisphenol sulfide, 3,3',5,5'-tetramethyl bisphenol sulfone, 3,3',5,5'-tetramethyl biphenol, 2,6-dibromo-3,3',5,5'-tetramethyl bisphenol F, 3,3',5,5'-tetramethyl-2,2',6,6'-tetrabromo biphenol, 1,1,1-tri-(hydroxyphenyl)alkanes, combinations thereof and the like. Suitable trihydroxyphenyl alkanes and method for their preparation can be found in U.S. Pat. No. 4,394,496 issued to Paul G. Schrader which is incorporated herein by reference.

Suitable alkali metal hydroxides and carbonates which can be employed herein include, for example, sodium hydroxide, potassium hydroxide, lithium hydroxide, sodium carbonate, potassium carbonate, combinations thereof and the like. The alkali metal hydroxide is employed in an amount of from about 0.95 to about 5, preferably from about 1 to about 2.5, most preferably from about 1 to about 1.5 moles per aromatic hydroxyl-group contained in the aromatic hydroxyl-containing material.

Suitable allyl halides which can be employed herein include, for example, allyl chloride, allyl bromide, allyl iodide, 2-methyl allyl chloride, 2-methyl allyl bromide, combinations thereof and the like. The allyl halide is employed in an amount of from about 0.95 to about 5, preferably from about 1 to about 2.5, most preferably from about 1 to about 1.5 moles per aromatic hydroxyl-group contained in the aromatic hydroxyl-containing material.

Suitable aprotic solvents which can be employed herein include, for example, dimethylformamide, dimethylsulfonamide, dimethylsulfoxide, N-methylpyrrolidinone, tetramethylene sulfone, hexamethyl phosphoramide, combinations thereof and the like.

The aprotic solvent can be employed in amounts of from about 25 to about 2000, preferably from about 50 to about 1000, most preferably from about 100 to about 500, percent by weight based upon the weight of the aromatic hydroxyl-containing material.

The reaction between the alkali metal hydroxide and/or the alkali metal carbonate and the aromatic hydroxyl-containing material can be conducted at any temperature of from about $-30°$ C. to about $120°$ C., preferably from about $0°$ C. to about $80°$ C., at a pressure which does not remove the solvent at the reaction temperature for a time sufficient to convert at least about 95, preferably at least about 98 of the aromatic hydroxyl groups to alkali metal phenoxide groups, usually from about 0.5 to about 20, preferably from about 1 to about 15, most preferably from about 2 to about 10, hours. The reaction between the resultant alkali metal phenoxide and the allyl halide can be conducted at a temperature of from about $0°$ C. to about $100°$ C., preferably from about $15°$ C. to about $60°$ C., at a pressure which does not remove the solvent at the reaction temperature and for a time sufficient to convert at least about 95, preferably at least about 98 percent of the alkali metal phenoxide groups to allyl groups, usually from about 0.5 to about 20, preferably from about 1 to about 15, most preferably from about 2 to about 10, hours.

The allyl ether product can be recovered by any suitable means known to those skilled in the art such as by distillation, water washing, precipitation, extraction, centrifugation, combinations thereof and the like.

Epoxidation of the allyl ether groups can be achieved by peroxidation with preformed peracid or by the insitu peroxidation method wherein the material containing the allyl ether groups are reacted with a monocarboxylic acid in the presence of hydrogen peroxide and catalyst at a temperature of from about $-40°$ C. to about $100°$ C., preferably from about $0°$ C. to about $80°$ C., most preferably from about $15°$ C. to about $70°$ C. for a time to convert essentially all of the allyl ether groups to glycidyl ether groups, usually from about 2 to about 80, preferably from about 5 to about 48, hours.

Suitable peracids include, for example, performic acid, peracetic acid, perbenzoic acid, m-chloroperbenzoic acid, combinations thereof and the like.

Suitable monocarboxylic acids include, for example, formic acid, acetic acid, propionic acid, benzoic acid, m-chlorobenzoic acid, combinations thereof and the like.

The resultant epoxy resins can be represented by the formulas I, II, III and IV wherein each A, A', X, Z, a, b, c, d, m and n are as defined above and each X' and X" is a glycidyl ether group. There may be present in the epoxy resin composition, very minor amounts of a material wherein X" is hydroxyl and a portion of the X groups is an allyl group.

The following examples are illustrative of the present invention but are not to be construed as to limiting the scope thereof in any manner.

EXAMPLE 1

General Procedure

To an indicated amount of solvent solution containing an indicated amount of o-cresol novolac resin having an average hydroxyl functionality of 6 was added an indicated amount of solid sodium hydroxide at room temperature ($\sim 25°$ C.). The mixture was stirred under a nitrogen atmosphere for the time indicated at the temperature indicated. After cooling the solution, the indicated amount of allyl chloride was slowly added at the temperature and over the time indicated. After completion of the allyl chloride, the reaction mixture was digested at the time and temperature indicated. The mixture was then cooled to room temperature (~25° C.). The solvent was then removed under a vacuum (10 mm Hg) and the indicated quantity of a solvent mixture was added to the syrupy residue. The solution was then washed several times with the indicated quantity of water until the pH was ~7. The organic layer was separated and concentrated under a vacuum. The yield and selectivity of the resultant allylated o-cresol novolac resin obtained, the reaction conditions, quantities of reactants and results are given in the following Table I.

TABLE I

| | A | B | C* | D* | D* |
|---|---|---|---|---|---|
| PREPARATION OF ALKALI METAL PHENOXIDE | | | | | |
| Solvent | | | | | |
| Type | DMF[3] | DMF | Methanol | Methanol | n-Propanol |
| milliliters | 1000 | 1200 | 700 | 250 | 500 |
| Novolac Resin | | | | | |
| grams | 236 | 236 | 118 | 59 | 59 |
| equiv. | 2 | 2 | 1 | 0.5 | 0.5 |
| Sodium Hydroxide | | | | | |
| grams | 120 | 172 | 86 | 43 | 43 |
| equiv. | 3 | 4 | 2 | 1 | 1 |
| Time, hours | 5 | 4 | 5–6 | 4 | 4 |
| , seconds | 18,000 | 14,400 | 18,000–21,600 | 14,400 | 14,400 |
| Temperature, °C. | 40 | 40 | 40–45 | 40 | 40 |
| ALLYLATION REACTION | | | | | |
| Allyl Chloride | | | | | |
| milliliters | 300 | 400 | 200 | 100 | 75 |
| equiv. | 4 | 4.9 | 2.45 | 1.22 | 1 |
| Addition | | | | | |
| Temp., °C. | 30–35 | 30–35 | 30–35 | 35 | 45 |
| Time, hours | 3–4 | 2 | 2 | 2 | 0.8 |
| , sec. | 10800–14400 | 7200 | 7200 | 7200 | 2880 |
| Digestion | | | | | |
| Temp., °C. | 35–40 | 35–40 | 35–40 | — | — |
| Time, hours | 4–6 | 1 | 6–8 | — | — |
| , sec. | 14,400–21,600 | 3600 | 21,600–28,800 | — | — |
| Digestion | | | | | |
| Temp., °C. | 40–45 | 40–45 | 40–45 | 40–45 | 55 |
| Time, hours | 4 | 5 | 6–7 | 1 | 5 |
| , sec. | 14,400 | 18,000 | 21,600–25,200 | 3600 | 18,000 |
| Digestion | | | | | |
| Temp., °C. | 55–60 | 50–55 | 50–55 | 50–55 | 60 |
| Time, hours | 2–4 | 3 | 3 | 12 | 6 |
| , sec. | 7200–14,400 | 10,800 | 10,800 | 43,200 | 21,600 |
| Solvent mixture added | | | | | |
| toluene, gms | 500 | 500 | 500 | 500 | 500 |
| methyl ethyl ketone, gms | 500 | 500 | 500 | 500 | 500 |
| Water Wash, ml/wash | 400 | 400 | 200 | 100 | 100 |
| PRODUCT CHARACTERISTICS | | | | | |
| Color | yellow brown | yellow brown | brown | brown | brown |
| Viscosity @ 25° C., cps | 4500 | 5000 | 4000–5000 | 4000–5000 | 4000–5000 |
| , Pa·s | 4.5 | 5.0 | 4–5 | 4–5 | 4–5 |
| Phenolic OH content, % | <0.03 | <0.03 | 1.34 | 1.27 | 1.54 |
| Total Chlorine, ppm | <50 | <170 | — | — | — |
| Ionic Chlorine, ppm | <2 | <8 | — | — | — |
| o-Allylation Components[1], % | >99 | >99 | 75 | 70 | 80 |
| c-Allylation Components[2], % | <1 | <1 | 25 | 30 | 18 |

*Not an example of the present invention.
[1]o-Allylation means that the hydroxyl group was allylated to an allyl ether group.
[2]c-Allylation means that the ring was allylated instead of the hydroxyl group.
[3]DMF is dimethylformamide.

We claim:

1. A process for preparing allyl ethers of aromatic hydroxyl-containing materials which comprises (A) reacting in the essential absence of water other than water produced in the reaction and in the presence of a polar aprotic solvent selected from the group consisting of dimethylformamide, dimethylacetamide, dimethyl sulfoxide, N-methyl pyrrolidinone, tetramethylene sulfone, hexamethyl phosphoramide, and a combination thereof (1) at least one material containing more than one aromatic hydroxyl group with (2) an alkali metal hydroxide, alkali metal carbonate or combination thereof at conditions sufficient to convert at least 95 percent of the aromatic hydroxyl groups to the corresponding alkali metal phenoxide group;

(B) reacting the reaction product mixture produced in (A) above with (3) at least one allyl halide at conditions sufficient to convert at least about 95 percent of the alkali metal phenoxide groups to an allyl ether group; and (C) thereafter recovering the resultant allyl ether product; and wherein component (2) is employed in a quantity which provides from about 0.95 to about 5 moles of component (2) per aromatic hydroxyl group contained in component (1) and component (3) is employed in a quantity which provides from about 0.95 to about 5 moles of component (3) per aromatic hydroxyl group contained in component (1).

2. A process of claim 1 wherein (a) step (A) is conducted at conditions sufficient to convert at least 98 percent of the aromatic hydroxyl groups to the corresponding alkali metal phenoxide group;

(b) the polar aprotic solvent is employed in an amount of from about 25 to about 2000 percent by weight based on the weight of component (1);

(c) component (2) is employed in a quantity which provides from about 0.95 to about 5 moles of component (2) per aromatic hydroxyl group contained in component (1); and (d) component (3) is employed in a quantity which provides from about 0.95 to about 5 moles of component (3) per aromatic hydroxyl group contained in component (1).

3. A process of claim 2 wherein (a) the polar aprotic solvent is employed in an amount of from about 50 to about 1000 percent by weight based on the weight of component (1);

(b) component (2) is employed in a quantity which provides from about 1 to about 2.5 moles of component (2) per aromatic hydroxyl group contained in component (1); and (c) component (3) is employed in a quantity which provides from about 1 to about 2.5 moles of component (3) per aromatic hydroxyl group contained in component (1).

4. A process of claim 3 wherein (a) the polar aprotic solvent is employed in an amount of from about 100 to about 500 percent by weight based on the weight of component (1);

(b) component (2) is employed in a quantity which provides from about 1 to about 1.5 moles of component (2) per aromatic hydroxyl group contained in component (1); and (c) component (3) is employed in a quantity which provides from about 1 to about 1.5 moles of component (3) per aromatic hydroxyl group contained in component (1).

5. A process of claim 1 wherein component (1) is a material represented by the following formulas I, II, III or IV or mixtures thereof

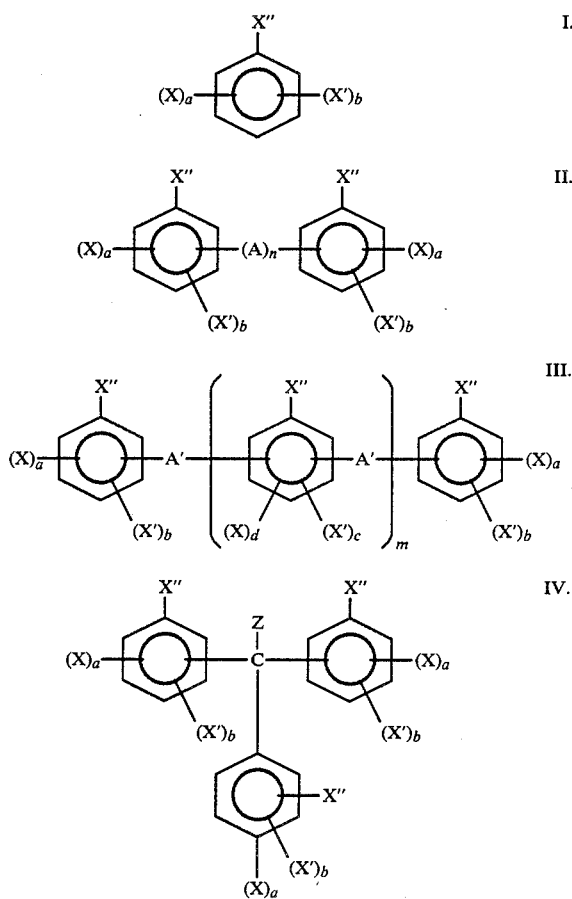

wherein A is a divalent hydrocarbyl group having from 1 to about 25 carbon atoms, a divalent dicyclopentadienyl group, a divalent oligomer of dicyclopentadiene, —O—, —S—, —S—S—,

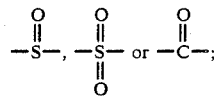

each A' is independently a divalent hydrocarbyl group having from 1 to about 25 carbon atoms, a divalent dicyclopentadienyl group or a divalent oligomer of dicyclopentadiene; each X is independently hydrogen, a hydrocarbyl or hydrocarbyloxy group having from 1 to about 10 carbon atoms or a halogen atom; X' is a hyroxyl group; X" is a hydroxyl group; Z is hydrogen or a hydrocarbyl group having from 1 to about 10 carbon atoms; each a independently has a value from about 1 to about 4; b and c each has a value of zero or 1; each d independently has a value of from 1 to 3; the sum of a+b is 4; the sum of d+c is 3; m has an average value from about zero to about 15 and n has a value of zero or 1.

6. A process of claim 5 wherein component (1) is a material represented by formulas (III) or (IV) wherein each A' is independently a divalent hydrocarbyl group having from 1 to about 10 carbon atoms or a divalent dicyclopentadienyl group; each X is independently hydrogen, a hydrocarbyl or hydrocarbyloxy group having from 1 to about 6 carbon atoms or a halogen atom; X' is a hyroxyl group; X" is a hydroxyl group; Z is hydrogen or a hydrocarbyl group having from 1 to about 6 carbon atoms; each a independently has a value from about 1 to about 4; b and c each has a value of zero or 1; each d independently has a value of from 1 to 3; the sum of a+b is 4; the sum of d+c is 3; and m has an average value from about zero to about 10; component (2) is sodium hydroxide, lithium hydroxide, potassium hydroxide, sodium carbonate, potassium carbonate or a combination thereof; and wherein component (3) is allyl chloride, allyl bromide, 2-methyl allyl chloride, 2-methyl allyl bromide or combination thereof.

7. A process of claim 6 wherein said polar aprotic solvent is dimethylformamide, dimethylsulfoxide or a combination thereof; component (1) is a material represented by formulas (III) or (IV) wherein each A' is independently a divalent hydrocarbyl group having from 1 to about 10 carbon atoms or a divalent dicyclopentadienyl group; each X is independently hydrogen, a hydrocarbyl or hydrocarbyloxy group having from 1 to about 6 carbon atoms or a halogen atom; X' is a hyroxyl group; X" is a hydroxyl group; Z is hydrogen or a hydrocarbyl group having from 1 to about 6 carbon atoms; each a independently has a value from about 1 to about 4; b and c each has a value of zero or 1; each d independently has a value of from 1 to 3; the sum of a+b is 4; the sum of d+c is 3; and m has an average value from about zero to about 10; component (2) is sodium hydroxide; component (3) is allyl chloride.

8. A process of claim 2 wherein component (1) is a material represented by the following formulas I, II, III or IV or mixtures thereof

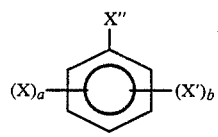

-continued

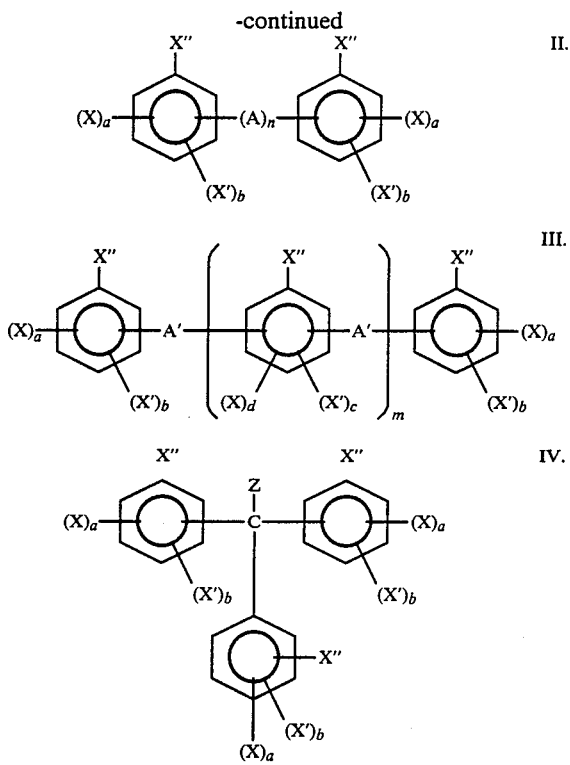

wherein A is a divalent hydrocarbyl group having from 1 to about 25 carbon atoms, a divalent dicyclopentadienyl group, a divalent oligomer of dicyclopentadiene, —O—, —S—, —S—S—,

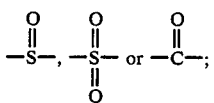

each A' is independently a divalent hydrocarbyl group having from 1 to about 25 carbon atoms, a divalent dicyclopentadienyl group or a divalent oligomer of dicyclopentadiene; each X is independently hydrogen, a hydrocarbyl or hydrocarbyloxy group having from 1 to about 10 carbon atoms or a halogen atom, preferably chlorine or bromine; X' is a hyroxyl group; X'' is a hydroxyl group; Z is hydrogen or a hydrocarbyl group having from 1 to about 10 carbon atoms; each a independently has a value from about 1 to about 4; b and c each has a value of zero or 1; each d independently has a value of from 1 to 3; the sum of a+b is 4; the sum of d+c is 3; m has an average value from about zero to about 15 and n has a value of zero or 1.

9. A process of claim 8 wherein component (1) is a material represented by formulas (III) or (IV) wherein each A' is independently a divalent hydrocarbyl group having from 1 to about 10 carbon atoms or a divalent dicyclopentadienyl group; each X is independently hydrogen, a hydrocarbyl or hydrocarbyloxy group having from 1 to about 6 carbon atoms or a halogen atom; X' is a hyroxyl group; X'' is a hydroxyl group; Z is hydrogen or a hydrocarbyl group having from 1 to about 6 carbon atoms; each a independently has a value from about 1 to about 4; b and c each has a value of zero or 1; each d independently has a value of from 1 to 3; the sum of a+b is 4; the sum of d+c is 3; and m has an average value from about zero to about 10; component (2) is sodium hydroxide, lithium hydroxide, potassium hydroxide, sodium carbonate, potassium carbonate or a combination thereof; and wherein component (3) is allyl chloride, allyl bromide, 2-methyl allyl chloride, 2-methyl allyl bromide or combination thereof.

10. A process of claim 9 wherein said polar aprotic solvent is dimethylformamide, dimethylsulfoxide or a combination thereof; component (1) is a material represented by formulas (III) or (IV) wherein each A' is independently a divalent hydrocarbyl group having from 1 to about 10 carbon atoms or a divalent dicyclopentadienyl group; each X is independently hydrogen, a hydrocarbyl or hydrocarbyloxy group having from 1 to about 6 carbon atoms or a halogen atom; X' is a hyroxyl group; X'' is a hydroxyl group; Z is hydrogen or a hydrocarbyl group having from 1 to about 6 carbon atoms; each a independently has a value from about 1 to about 4; b and c each has a value of zero or 1; each d independently has a value of from 1 to 3; the sum of a+b is 4; the sum of d+c is 3; and m has an average value from about zero to about 10; component (2) is sodium hydroxide; component (3) is allyl chloride.

11. A process of claim 3 wherein component (1) is a material represented by the following formulas I, II, III or IV or mixtures thereof

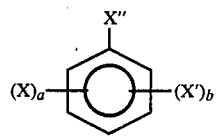

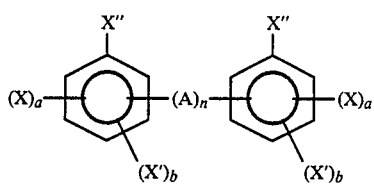

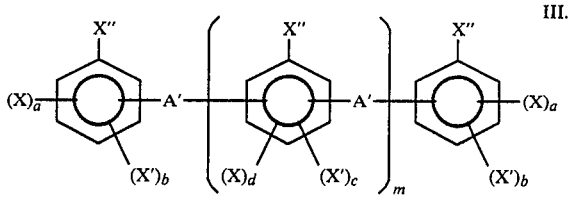

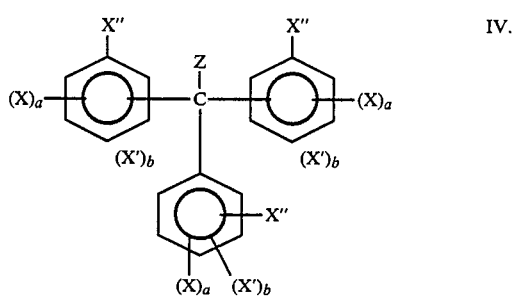

wherein A is a divalent hydrocarbyl group having from 1 to about 25 carbon atoms, a divalent dicyclopentadienyl group, a divalent oligomer of dicyclopentadiene, —O—, —S—, —S—S—,

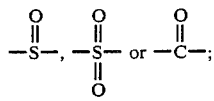

each A' is independently a divalent hydrocarbyl group having from 1 to about 25 carbon atoms, a divalent dicyclopentadienyl group or a divalent oligomer of dicyclopentadiene; each X is independently hydrogen, a hydrocarbyl or hydrocarbyloxy group having from 1 to about 10 carbon atoms or a halogen atom, preferably chlorine or bromine; X' is a hyroxyl group; X" is a hydroxyl group; Z is hydrogen or a hydrocarbyl group having from 1 to about 10 carbon atoms; each a independently has a value from about 1 to about 4; b and c each has a value of zero or 1; each d independently has a value of from 1 to 3; the sum of a+b is 4; the sum of d+c is 3; m has an average value from about zero to about 15 and n has a value of zero or 1.

12. A process of claim 11 wherein component (1) is a material represented by formulas (III) or (IV) wherein each A' is independently a divalent hydrocarbyl group having from 1 to about 10 carbon atoms or a divalent dicyclopentadienyl group; each X is independently hydrogen, a hydrocarbyl or hydrocarbyloxy group having from 1 to about 6 carbon atoms or a halogen atom; X' is a hydroxyl group; X" is a hydroxyl group; Z is hydrogen or a hydrocarbyl group having from 1 to about 6 carbon atoms; each a independently has a value from about 1 to about 4; b and c each has a value of zero or 1; each d independently has a value of from 1 to 3; the sum of a+b is 4; the sum of d+c is 3; and m has an average value from about zero to about 10; component (2) is sodium hydroxide, lithium hydroxide, potassium hydroxide, sodium carbonate, potassium carbonate or a combination thereof; and wherein component (3) is allyl chloride, allyl bromide, 2-methyl allyl chloride, 2-methyl allyl bromide or combination thereof.

13. A process of claim 12 wherein said polar aprotic solvent is dimethylformamide, dimethyl sulfoxide or a combination thereof; component (1) is a material represented by formulas (III) or (IV) wherein each A' is independently a divalent hydrocarbyl group having from 1 to about 10 carbon atoms or a divalent dicyclopentadienyl group; each X is independently hydrogen, a hydrocarbyl or hydrocarbyloxy group having from 1 to about 6 carbon atoms or a halogen atom; X' is a hyroxyl group; X" is a hydroxyl group; Z is hydrogen or a hydrocarbyl group having from 1 to about 6 carbon atoms; each a independently has a value from about 1 to about 4; b and c each has a value of zero or 1; each d independently has a value of from 1 to 3; the sum of a+b is 4; the sume of d+c is 3; and m has an average value from about zero to about 10; component (2) is sodium hydroxide; component (3) is allyl chloride.

14. A process of claim 4 wherein component (1) is a material represented by the following formulas I, II, III or IV or mixtures thereof

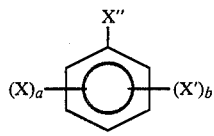

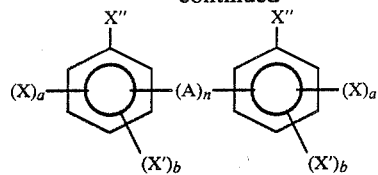

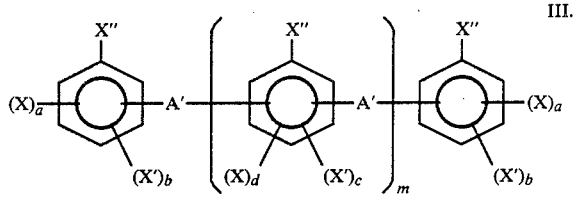

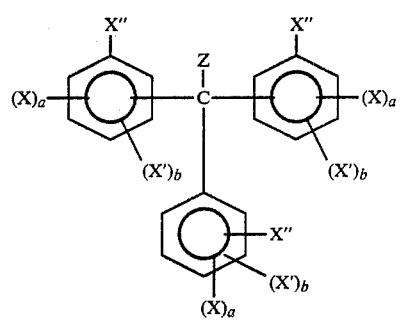

wherein A is a divalent hydrocarbyl group having from 1 to about 25 carbon atoms, a divalent dicyclopentadienyl group, a divalent oligomer of dicyclopentadiene, —O—, —S—, —S—S—,

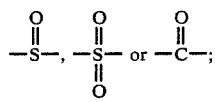

each A' is independently a divalent hydrocarbyl group having from 1 to about 25 carbon atoms, a divalent dicyclopentadienyl group or a divalent oligomer of dicyclopentadiene; each X is independently hydrogen, a hydrocarbyl or hydrocarbyloxy group having from 1 to about 10 carbon atoms or a halogen atom, preferably chlorine or bromine; X' is a hyroxyl group; X" is a hydroxyl group; Z is hydrogen or a hydrocarbyl group having from 1 to about 10 carbon atoms; each a independently has a value from about 1 to about 4; b and c each has a value of zero or 1; each d independently has a value of from 1 to 3; the sum of a+b is 4; the sum of d+c is 3; m has an average value from about zero to about 15 and n has a value of zero or 1.

15. A process of claim 14 wherein component (1) is a material represented by formulas (III) or (IV) wherein each A' is independently a divalent hydrocarbyl group having from 1 to about 10 carbon atoms or a divalent dicyclopentadienyl group; each X is independently hydrogen, a hydrocarbyl or hydrocarbyloxy group having from 1 to about 6 carbon atoms or a halogen atom; X' is a hyroxyl group; X" is a hydroxyl group; Z is hydrogen or a hydrocarbyl group having from 1 to about 6 carbon atoms; each a independently has a value from about 1 to about 4; b and c each has a value of zero or 1; each d independently has a value of from 1 to 3; the sum of a+b is 4; the sum of d+c is 3; and m has an average value from about zero to about 10; component (2) is sodium hydroxide, lithium hydroxide, potassium hydroxide, sodium carbonate, potassium carbonate or a combination thereof; and wherein component (3) is allyl chloride, allyl bromide, 2-methyl allyl chloride, 2-methyl allyl bromide or combination thereof.

16. A process of claim 15 wherein said polar aprotic solvent is dimethylformamide, dimethyl sulfoxide or a combination thereof; component (1) is a material represented by formulas (III) or (IV) wherein each A' independently a hydrocarbyl group having from 1 to about 10 carbon atoms or a divalent dicyclopentadienyl group; each X is independently hydrogen, a hydrocarbyl or hydrocarbyloxy group having from 1 to about 6 carbon atoms or a halogen atom; X' is a hyroxyl group; X" is a hydroxyl group; Z is hydrogen or a hydrocarbyl group having from 1 to about 6 carbon atoms; each a independently has a value from about 1 to about 4; b and c each has a value of zero or 1; each d independently has a value of from 1 to 3; the sum of a+b is 4; the sum of d+c is 3; and m has an average value from about zero to about 10; component (2) is sodium hydroxide; component (3) is allyl chloride.

* * * * *

UNITED STATES PATENT AND TRADEMARK OFFICE
CERTIFICATE OF CORRECTION

PATENT NO. : 4,740,330

DATED : April 26, 1988

INVENTOR(S) : Chun S. Wang, Zeng-kun Liao

It is certified that error appears in the above-identified patent and that said Letters Patent is hereby corrected as shown below:

Col. 3, line 1; insert --a-- between "each" and "independently".

Col. 11, line 55; change "sume" to --sum--.

Col. 13, line 9; insert --is-- between "A" and "inde-".

UNITED STATES PATENT AND TRADEMARK OFFICE
CERTIFICATE OF CORRECTION

PATENT NO. : 4,740,330

DATED : April 26, 1988

INVENTOR(S) : Chun S. Wang, Zeng-kun Liao

It is certified that error appears in the above-identified patent and that said Letters Patent is hereby corrected as shown below:

In Claims 8 and 11, replace the Formula IV with the following Formula IV:

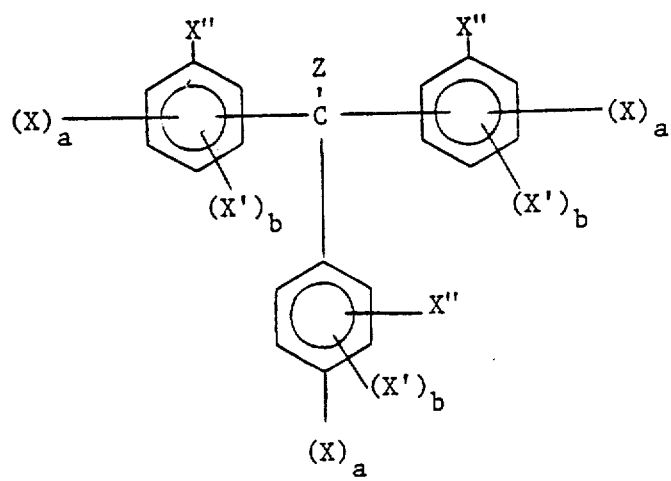

Signed and Sealed this

Twenty-ninth Day of November, 1988

*Attest:*

DONALD J. QUIGG

*Attesting Officer*  *Commissioner of Patents and Trademarks*